United States Patent [19]
Gilchrist

[11] Patent Number: 6,024,854
[45] Date of Patent: Feb. 15, 2000

[54] METHOD AND APPARATUS FOR IMPROVING ELECTROPHORESIS RESOLUTION

[75] Inventor: Rodney D. Gilchrist, Oakville, Canada

[73] Assignee: Visible Genetics, Inc., Toronto, Canada

[21] Appl. No.: 09/096,227

[22] Filed: Jun. 11, 1998

[51] Int. Cl.[7] .................................................. G01N 27/26
[52] U.S. Cl. .......................................... 204/466; 204/616
[58] Field of Search ................................... 204/456, 606, 204/616, 466

[56] References Cited

U.S. PATENT DOCUMENTS

| | | |
|---|---|---|
| 4,908,112 | 3/1990 | Pace . |
| 5,104,512 | 4/1992 | Gombocz et al. ....................... 204/607 |
| 5,217,591 | 6/1993 | Gombocz et al. ....................... 204/466 |
| 5,328,578 | 7/1994 | Gordon . |
| 5,549,796 | 8/1996 | Chu et al. . |
| 5,833,826 | 11/1998 | Nordman . |

Primary Examiner—Jill Warden
Assistant Examiner—Alex Noguerola
Attorney, Agent, or Firm—Oppedahl & Larson LLP

[57] ABSTRACT

Electrophoretic separation of an analyte species in a sample is achieved with increased resolution by loading the sample onto a loading site of an electrophoresis gel, said loading site having a gel/buffer interface and then applying a focusing electric field to a first pair of electrodes to cause the analyte species to migrate to a narrow region disposed at or near the loading site to produce a focused sample. Then a separation electric field is applied to cause the analyte species in the focused sample to migrate through the electrophoresis gel and to be separated into bands. This method is preferably performed in an electrophoresis apparatus that is particularly adapted to practicing the method by virtue of the a pair of focusing electrodes which are positioned to cause migration of sample to a narrow region near the buffer/gel interface within the sample loading site of the gel. This actual location of this narrow region may be in a buffer region over the gel, or just within the gel near the loading site, for example within 500 microns of the loading site.

16 Claims, 7 Drawing Sheets

METHOD AND APPARATUS FOR IMPROVING ELECTROPHORESIS RESOLUTION

This application relates to a method and apparatus for performing electrophoresis, and in particular for performing gel electrophoresis.

Gel electrophoresis is an important part of many nucleic acid sequencing procedures. In the basic sequencing procedures, mixtures of labeled sequencing fragments differing in length by as little as one base and rarely by more than three or four bases are loaded onto a gel and caused to migrate by an electric field imposed on the gel. Resolution of the mixture into identifiable bands corresponding to fragments of a given length is necessary for effective determination of the sequence. The ability of an electrophoresis system to resolve fragments of different sizes into separate, identifiable bands depends on two factors: the physical separation that can be achieved between the center of two adjacent bands and on the width of the band.

When an electric field is first applied to a charged species in a gel, that species is accelerated to a terminal velocity which is roughly (ignoring secondary effects) proportional to the applied electric field and to the mobility of the charged species in the medium. Larger fragments have a lower terminal velocity, the terminal velocity of one fragment being related to another by a 1/N relationship, where N is the size of the fragment in bases. This relationship means that there is less difference in terminal velocity between two larger fragments than there is between two smaller fragments. The practical effect of this relationship is a gradual decrease in the physical separation between adjacent bands with increasing fragment length.

The width of the band at the point that it is measured is more complicated, and is a consequence of a combination of factors including the injection phenomena such as the time interval over which fragments enter the gel, and the shape of the top surface of the gel; diffusional spreading during migration; and velocity differences due to transverse temperature variation in the gel during band migration. It is the object of the present invention to provide a method and apparatus which provides improved resolution by mitigating the impact of injection phenomena on band width.

SUMMARY OF THE INVENTION

This and other objects are achieved using a method for electrophoretic separation of analyte species in a sample, comprising the steps of:
  (a) loading the sample onto a loading site of an electrophoresis gel;
  (b) applying a focusing electric field to a first pair of electrodes to cause the analyte species to migrate to a narrow region disposed at or near the loading site;
  (c) applying a separation electric field to cause the analyte species in the focused sample to migrate through the electrophoresis gel and to be separated into bands. This method is preferably performed in an electrophoresis apparatus that is particularly adapted to practicing the method by virtue of the a pair of focusing electrodes which are positioned to cause migration of sample to a narrow region near the buffer/gel interface within the sample loading site of the gel. This actual location of this narrow region may be in the buffer or just within the gel near the loading site.

DETAILED DESCRIPTION OF THE INVENTION

The present invention is directed to a method and apparatus for improving the resolution of a gel electrophoresis system. As used in the specification and claims hereof, the term "resolution" is defined as the distance between the centers of two adjacent bands being separated divided by the width of the bands. In the context of nucleic acid sequencing, improvement of resolution allows determination of more bases pairs in a single experimental run, and can be traded off to shorten separation times, both of which increase instrument throughput and thus lower the cost of analysis.

In accordance with the invention, improved resolution is achieved by controlling the injection width through the use of a set of focusing electrodes disposed at the injection point. Thus, in the method of the invention electrophoresis is performed in two steps, a first step in which the sample is focused using the focusing electrodes into a first incrementally narrow portion of the gel, and a second step in which the focused sample is caused to migrate through the gel to form separate detectable bands.

The focusing of the sample prior to the main separation step is performed using a pair of electrodes which are positioned to cause migration of sample to a narrow region near the buffer/gel interface within the sample loading site of the gel. This actual location of this narrow region may be in the buffer or entirely within the gel near the loading site (i.e., within about 500 microns of the buffer/gel interface, depending on the location of the electrodes). Several variations of an apparatus in accordance with the invention which localize the sample for injection at these various sites are illustrated in the embodiments of the invention shown in the figures.

Figure 1A:
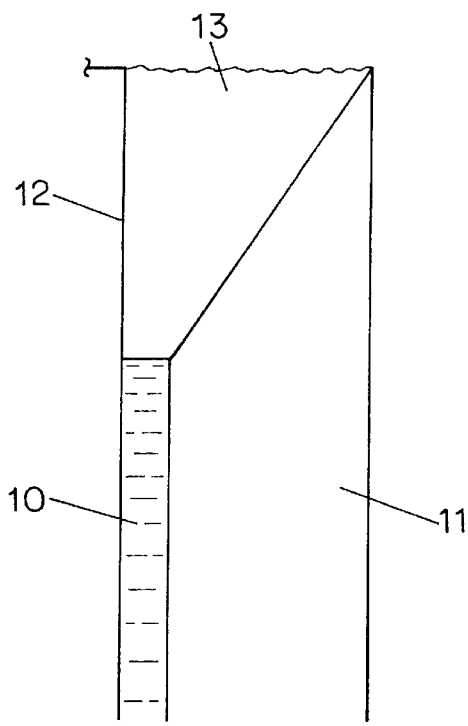
FIGS. 1A–D show cross-sections of a top of an electrophoresis gel having a prismatic sample loading well, and illustrate various locations for placement of the focusing electrodes.

FIGS. 1A–D show cross-sections of a top of an electrophoresis gel having a prismatic sample loading well, and illustrate various locations for placement of the focusing electrodes. FIG. 1A shows the parts of this region of the gel, without focusing electrodes, and thus represents the prior art. The gel 10, for example having a thickness of around 50 microns, is formed between two parallel substrates (for example glass or plastic plates) 11 and 12. A beveled cut at the top of substrate 12 creates a prismatic well which is filled with buffer 13. Electrodes disposed in contact with the buffer 13 and with the bottom of the gel (not shown) are used to create an electric field in which analyte species in the sample will migrate.

Figure 1B:
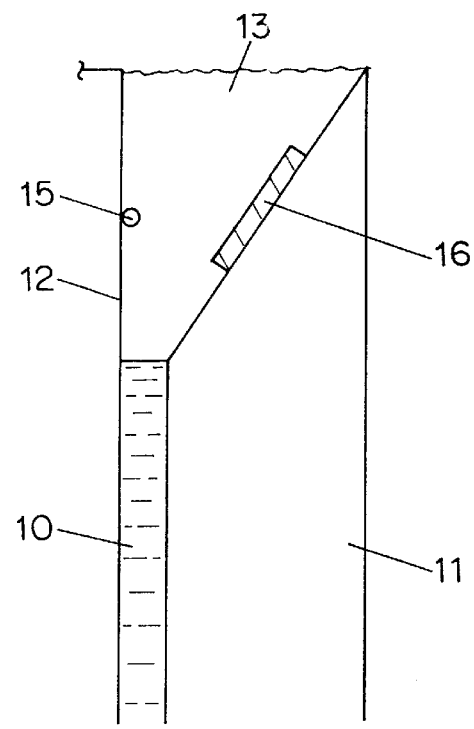
Figure 1C:
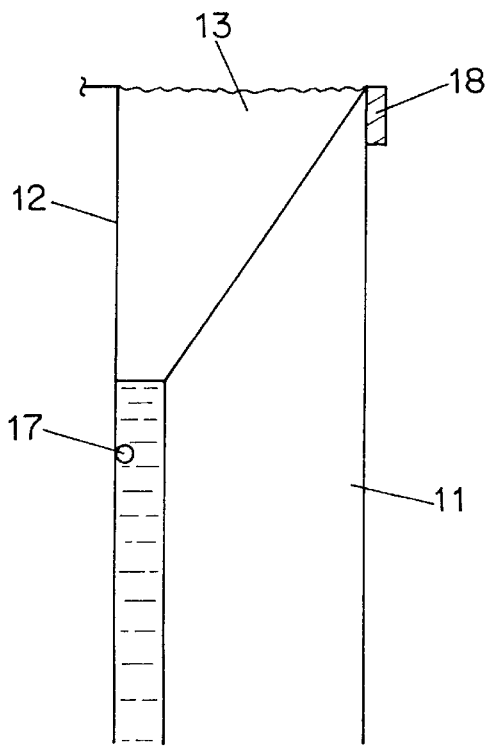
Figure 1D:
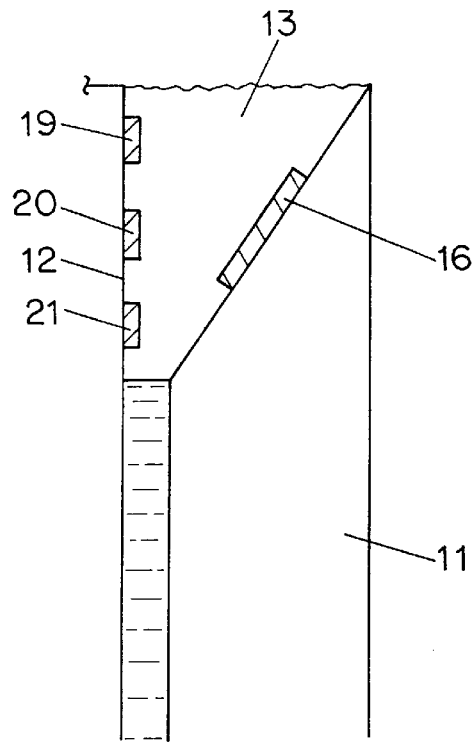

FIG. 1B shows an electrophoresis gel in accordance with the invention in which the focusing electrodes include an electrode 15 disposed on or near the vertical face of the prismatic sample well, and a planar electrode 16 disposed on the angled surface of the sample well. In FIG. 1C, focusing electrodes include a electrode 17 disposed just below the gel/buffer interface within the gel, and a planar electrode 18 disposed at the top of the angled surface of the sample well in contact with the buffer 13. In the FIG. 1D, the focusing electrodes include three electrodes 19, 20, and 21 on or near the vertical face of the prismatic sample well, and a planar electrode 16 disposed on the angled surface of the sample well. To accomplish focusing, an electric field is generated between electrodes 15 and 16, between electrodes 17 and 18, or between electrodes 19, 20 and 21, and electrode 16. Other combinations of the electrode locations shown in FIGS. 1B–1D can be used, and these specific combinations are merely provided by way of example.

It will be appreciated that placement of two focusing electrodes within the sample loading well or the adjacent gel is not necessary to practicing the method of the present invention, because the top separation electrode may be used in combination with a single focusing electrode disposed near the gel/buffer interface (either in the buffer filled loading well or within the gel itself). Thus, neither of the focusing electrodes at or near the loading site is used to apply the separation electric field.

The focusing electrodes of the invention may be formed from wire, for example platinum wire disposed at the desired location within the electrophoresis gel. Platinum is preferred over copper or tinned copper wire which are eroded by electrochemical action at the voltages normally used for DNA sequencing. The electrodes may also be formed by printing or plating a conductive material that is stable under the conditions used for separating DNA sequencing fragments. Exemplary methods of forming electrodes include screened conductive ink with 100 nanometers or so of gold electroplated onto it; vacuum deposited gold 100 to 500 nanometers thick; vacuum deposited indium-tin oxide with gold electroplated on and vacuum deposited indium-tin oxide with a protective layer such as vacuum deposited silicon dioxide, a surface pacification layer or other protective layer. This latter electrode is different from the other electrodes types because movement of the sample will be based on the field and not current. In the case of movement based on current, it is important that the electrodes not react or decompose in the environment either of the buffer/gel interface or in the gel itself.

Regardless of the method of formation of the electrodes, when they are disposed on the surface of the substrate, they will generally be formed such that analyte cannot migrate between the electrode and the near-by substrate. However, it is contemplated that the electrodes could be suspended or positioned above the substrate within the sample loading near or within the sample loading well or within the gel by means of a self-supporting electrode (i.e,. a wire electrode) or a non-conductive support member (e.g. a metal strip coated with a non-conductive coating (i.e., TEFLON), or a plastic or glass strip or fiber.

The electrodes are used to generate a field of 5 Volts/cm or higher, in order to overcome convective motion within the sample well. In general, fields from about 10 Volts/cm to about 40 Volts/cm are preferred. This is compared with the normal running field strength of 100 Volts/cm. In generating this field strength, a voltage below 1.7 volts should be used to avoid electrolysis of water and concomitant bubble formation.

If the distance between the electrodes is too large to achieve the desired field strength with this voltage restriction, several electrodes (such as those shown in FIG. 1D) can be used in successive stages. For example, a higher voltage (e.g. 10 V) might be applied to electrode 19 and 16 which would cause formation of bubbles, but which would also substantially concentrate charged materials in the buffer near electrode 16. Then, in a second stage of the process, a lower voltage is used to produce a field between electrodes 16 and 20 to form the sample into a small volume without convective disturbance caused by the bubbles. Then, in a third stage, a lower voltage is used to produce a field between electrodes 20 and 21 to refocus the sample to a small volume near electrode 21.

Figure 2:
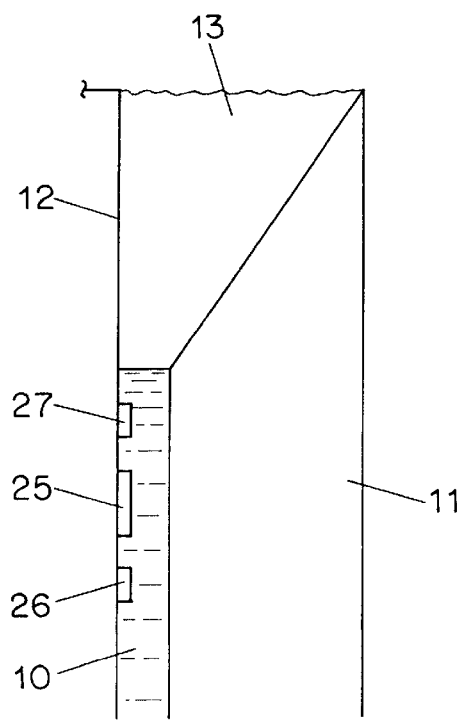
FIG. 2 shows the placement of electrodes in an embodiment of the invention.

FIG. 2 shows an embodiment of the invention in which the focusing electrodes are disposed on the inner surface of electrophoresis gel 10 in the area of the loading well. Electrodes 25 and 26 are two electrodes of differing surface area. A third electrode 27 may be disposed above electrode 25. The purpose of having a series of differing sized focusing electrodes is to move the DNA fragments in stages, between electrode 27 to the surface of electrode 25 (a wide electrode), and then to electrode 26. In this embodiment, after the DNA is drawn to electrode 25, electrode 27 is deactivated and electrode 26 is given a charge such that the DNA fragments move from electrode 25 to electrode 26 (note electrode 26 has less surface area than electrode 25 which focuses or concentrates the DNA fragments from the wider areas of electrode 25 to the narrower area of electrode 26. As a result, the DNA fragments are concentrated in a stepwise fashion by using pairs of electrodes.

The advantage of using sets of electrodes to concentrate the DNA in steps is that it allows a large, low resistance electrode to sweep the DNA from a 'large' volume and then a fine geometry second electrode to provide further focusing quickly due to its closeness to the first electrode (and the consequent high field strength between two closely-spaced electrodes.)

Figure 3:
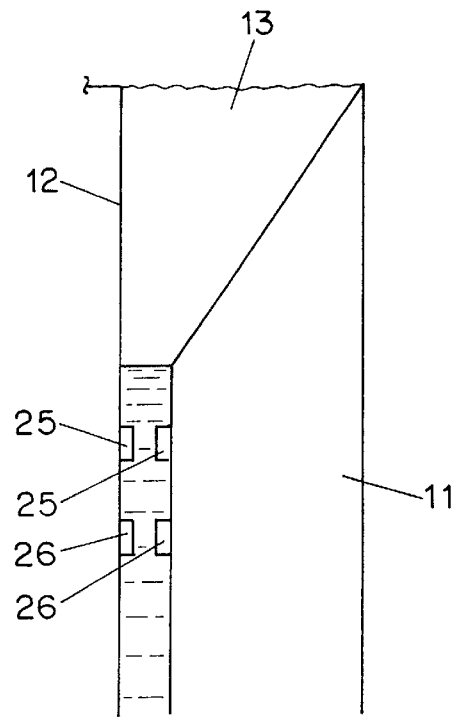
FIG. 3 shows the placement of electrodes in a further embodiment of the invention.

FIG. 3 is a variation on FIG. 2 showing pairs of parallel electrodes on opposing inner surfaces in the gel loading well. For example, they could be two electrodes 25 and two electrodes 26. As the DNA molecules move near the leading edges of the 26 electrodes (on diagram, from top of page to bottom), the field strength drops off, which results in the DNA stopping between electrodes 26. This positions the DNA in the middle of the gel volume, rather than being pulled to the edge of the gel as in the embodiment of FIG. 2. The DNA is thus ready to migrate under the field between the main electrode (bottom of gel, not shown) and the 26 electrodes while minimizing potential distortion in the band that can result from its proximity to the surface of the gel.

Figure 4:
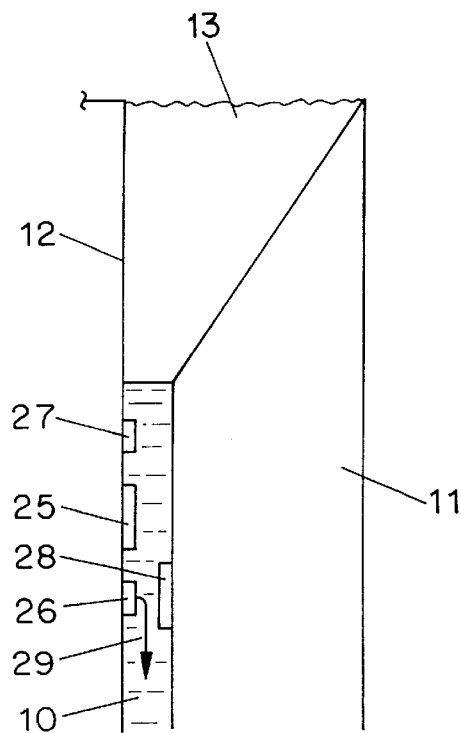
FIG. 4 shows the placement of electrodes in a further embodiment of the invention.

FIG. 4 shows a further embodiment of a gel in accordance with the invention in which a further electrode 28 is disposed opposite to electrode 26. Initially, the DNA fragments migrate from 27 to 25, and then from 25 to 26 as described in connection with FIG. 2 above to achieve focusing. Then, when the electrophoretic run begins, the electrode at the bottom of the gel (not shown) and 28 are both charged with the same charge, opposite to 25 (or other separation electrode disclosed above electrode 25. This causes the DNA fragments to move away from the surface of electrode 26 as they begin to migrate in a trajectory as indicated by the arrow 29. Thus, this configuration also permits centering of the migrating bands to provide improved band quality.

Figure 5A:
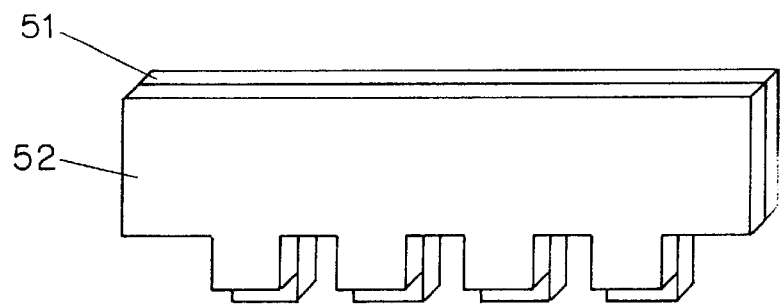
FIGS. 5A and 5B show an embodiment of electrode assembly in accordance with the invention.
Figure 5B:
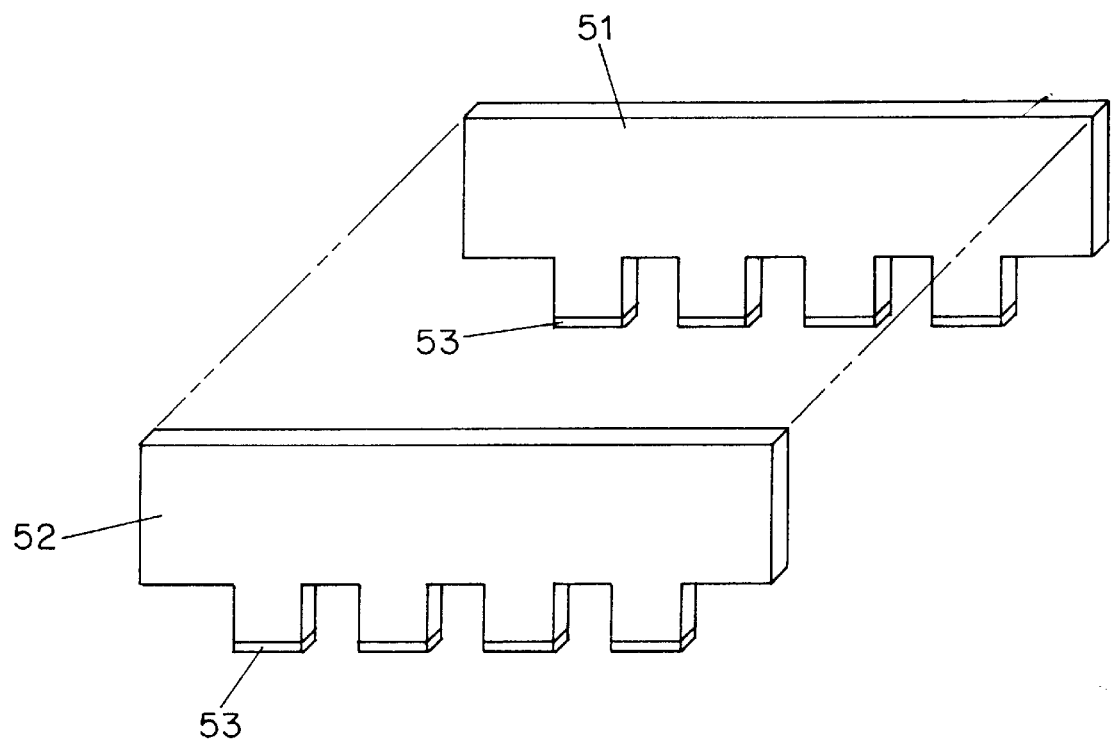
Figure 6:
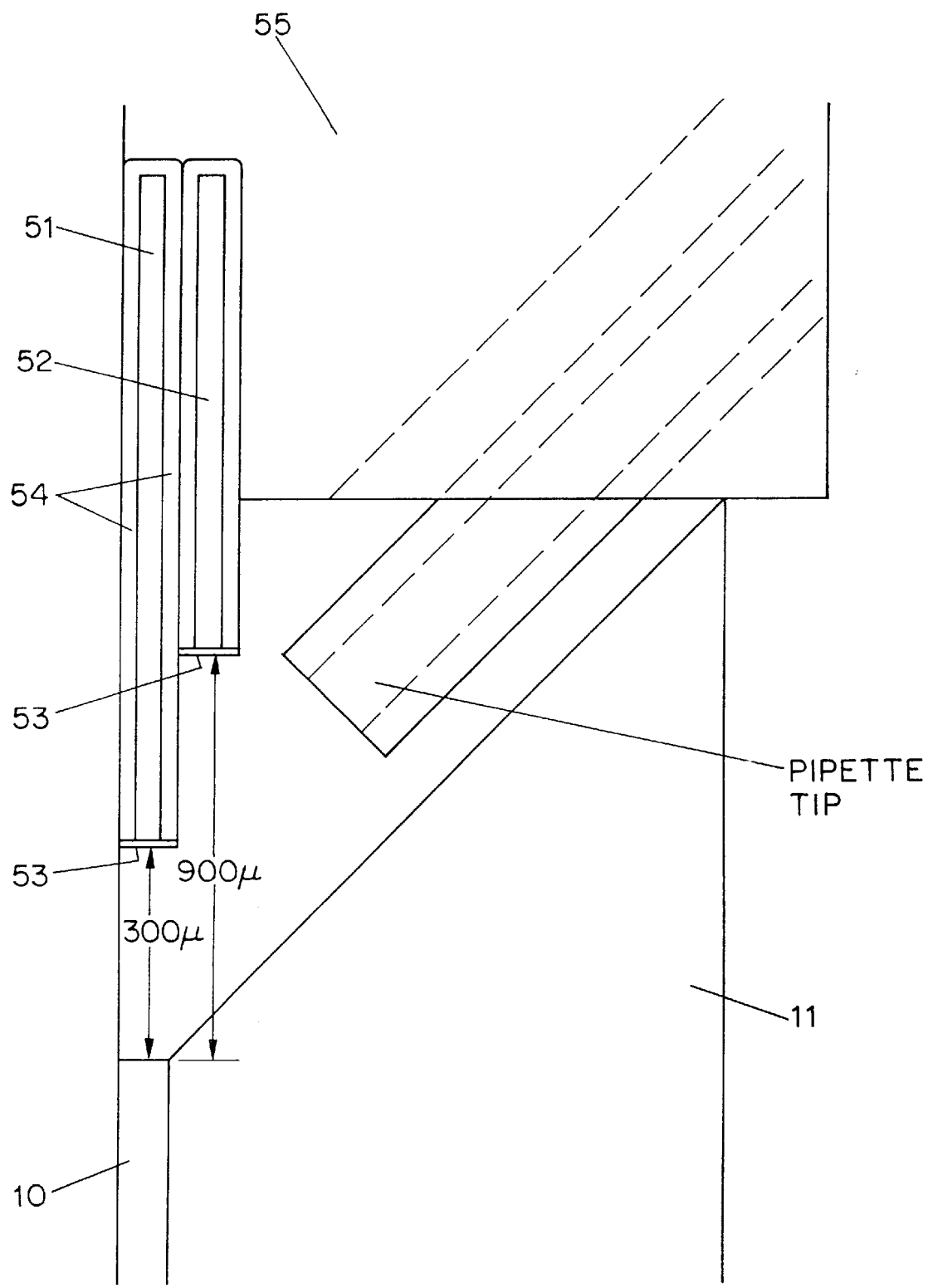
FIG. 6 shows the electrode of FIGS. 5A and 5B within the loading well of an electrophoresis gel.

The method of the invention is preferably practiced using an electrophoresis gel which incorporates a removable electrode system which may be made as either a reusable or a disposable component. FIGS. 5A and 5B and 6 show an embodiment of such a system.

To make the system shown in FIGS. 5A and B, a thin conductive plate, (e.g., 25 micron (0.001 inch) shim stock) is die cut in the shape of the outline of the plug used in molding sample wells in the gel. A wire is then attached to one of the top corners of the die cut plate via soldering or spot welding. The die cut plate 51 is then coated with an insulating material 54 with a coating 10 or 20 microns thick. A thicker coating may be used in the area of the wire attachment for reinforcement if desired. The bottom end of the coated plate is then cut off, leaving the interior conductive plate exposed. A gold layer 53 is electroplated onto the exposed metal surface of the plate. This plate can be used in combination with the main electrophoresis electrode, or it can be used with a second focusing electrode of similar construction.

When a second focusing electrode is used, a second plate 52 is prepared similarly. The two plates are then glued together (aligned so that the gold electrode surface of the second plate is about 600 microns higher than the first plate). Optionally, the second plate does not have to have a notched edge, as in the first plate, although it may fit better within the individual sample wells if it is. In any event, the two electrodes wshould be sufficiently close to one another (i.e, within about 1 mm in most electrophoresis media) to obtain an adequate electric field.

In either the one or two electrode configuration, a 1–2 mm thick plastic stiffener 55 is attached to the top. When used in a gel holder with a beveled opening such as a Visible Genetics MICROCEL electrophoresis gel holder, the plastic stiffener fits down so that it touches the top edge of the bevel of the sample well as shown in FIG. 6 (e.g. the lower surface of the plastic stiffener is about 100 microns above the higher of the two electrodes). The plastic stiffener and serves the secondary purpose of helping to contain sample in the sample well. At each sample well position the stiffener has an angled guide slot for the pipette tip for loading of samples, and at the edge of the slot it has relatively small escape channels for buffer that is displaced during sample loading.

To use the electrode system of FIG. 5A and 5B and 6, after filling the gel in the normal manner the plug used for forming sample wells is removed, and the electrode system is placed in the wells. First, 1.5 volts is then applied between the two electrodes within the sample well, and then sample is loaded with a pipette through the guide slot. The edge of each respective electrode is about 300 and 900 microns from the nominal gel surface. Thus, at least one focusing electrode is disposed within the loading well or within the separation medium within 500 microns of the loading well.

The lower electrode collects the DNA in the sample (quickly due to the 30 V/cm field) against the smooth lower surface (approximately 300 microns from the gel surface), forming the sample into a thin (e.g. 1 to 10 microns thick ), flat layer. The sample now has an ideal position, orientation and thickness with respect to how it will travel in the gel. When the main electrophoresis voltage is applied the sample thickness is further compressed by the speed change that occurs as it crosses the buffer-gel boundary.

Figure 7:
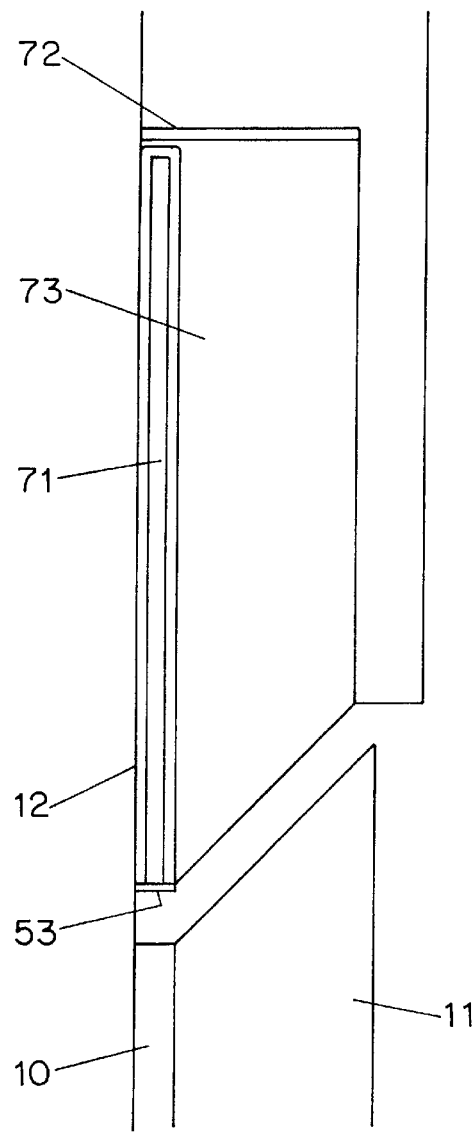
FIG. 7 shows a further embodiment of an electrode assembly according to the invention.

FIG. 7 shows a further embodiment of an electrode system in accordance with the invention. In this case, the electrode assembly is formed from two electrodes 71, 72 separated by a porous insert 73 which is used to absorb the sample. Suitable porous materials for use as the absorptive sample collection member in electrodes in accordance with the invention include paper or polymer wick materials, capillaries or other materials that can absorb a liquid sample. In use, the whole electrode assembly is dipped in sample (e.g. a microtiter plate). The sample is drawn up into the porous insert and then the assembly is inserted into the sample wells on the gel. The electrode potential drives charged species in the sample out of the porous insert, concentrating them around the second electrode. The main electrodes are then activated to begin the electrophoresis run. This avoids the necessity of pipetting the samples manually into the sample wells. Further, without manual pipetting, smaller lanes may be used therefore increasing the number of samples which can be run. In addition, the use of a porous or capillary comb permits the loading step to be automated. A robot could pick up a loader comb, insert it into a micro titre well plate to load the samples, then insert the comb into the gel.

The strength of the capillary action can also be chosen to determine the sample volume which is picked up ( ie: density of the porous material (porus paper vs fine fibre paper) or the internal diameter and length of the capillary). For example, in the case of the Visible Genetics MICROGENE BLASTER or MICROGENE CLIPPER sequencers, each capillary would have to pick up 2 ul, which is the volume currently pipetted manually into each loading well.

Figure 8:
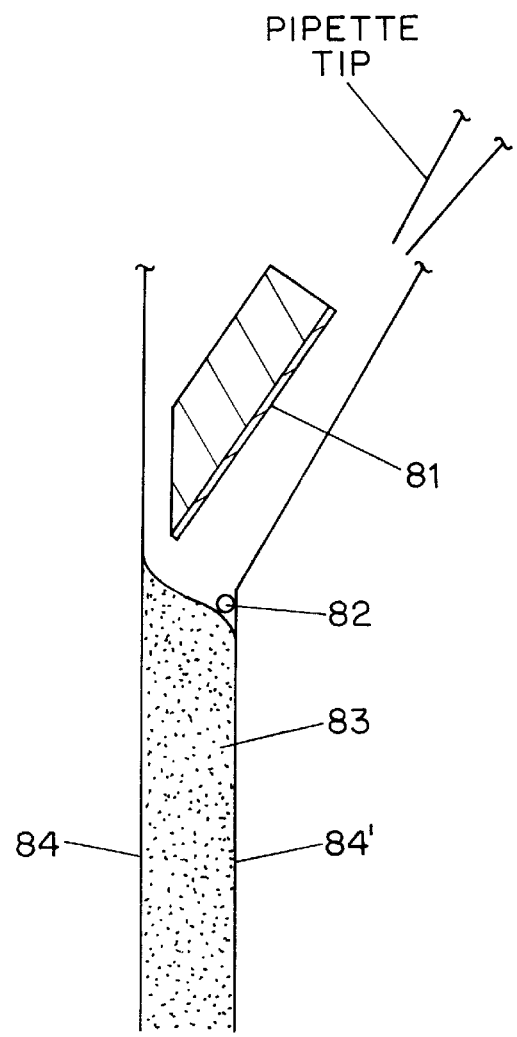
FIG. 8 shows a further embodiment of an electrode assembly according to the invention.

FIG. 8 shows another example of focusing electrodes with one electrode 81 located on the well of a MICROCEL and the other 82 located within the line of adhesive 83 which holds the two plates 84, 84' of the MICROCEL together and separates individual lanes. Electrode 81 is a fiberglass sheet coated with copper (at 20 oz/square foot thickness) which is further coated with 2 to 3 um of gold. This electrode is placed so that the gold surface is spaced approximately 1.5 mm from the upper beveled surface of the MICROCEL's loading well. The second electrode 82 is a copper wire plated with 25 um thickness of gold. This wire electrode is positioned perpendicular to the lanes and is held by adhesive 83 (part of the adhesive bead used to define the lanes and hold the glass plates together) adjacent to the gel. The MICROCEL has a gel thickness of 20 um.

Figure 9:
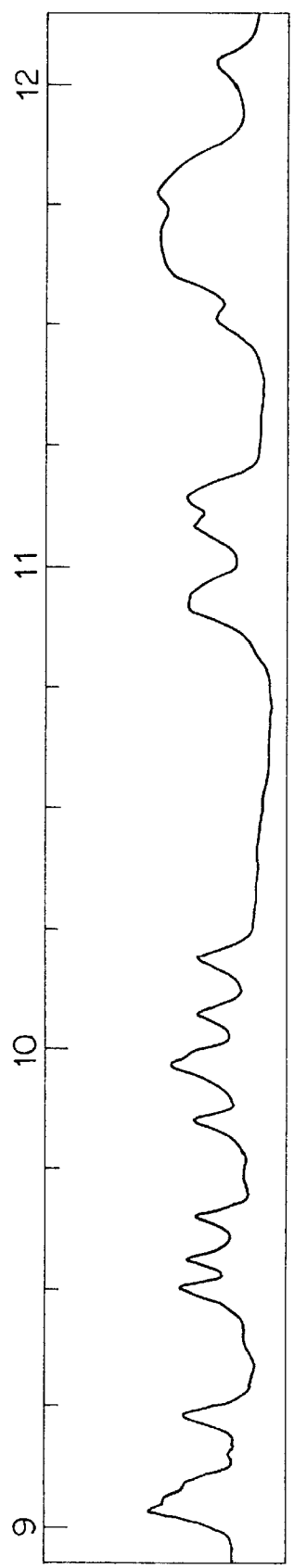
FIGS. 9 and 10 shows comparative electrophoretic separation patterns obtained in without application and with application of a preliminary focusing voltage gradient.
Figure 10:
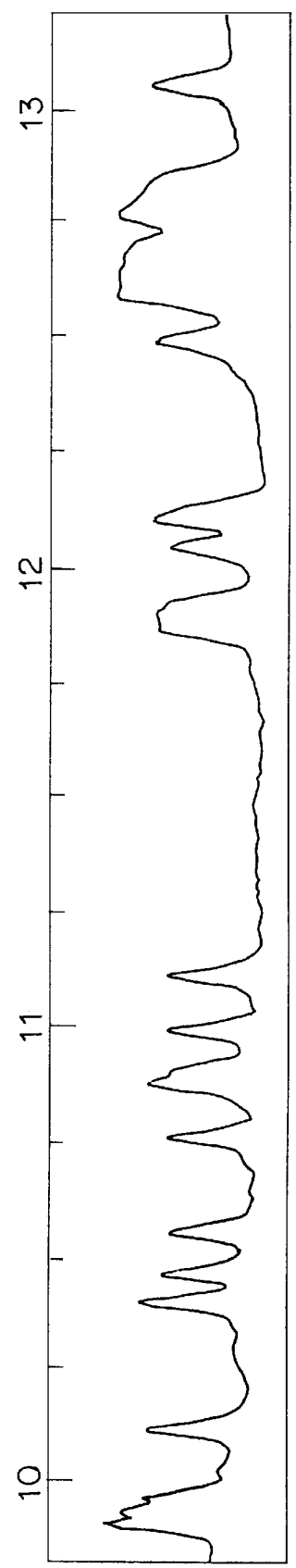

FIGS. 9 and 10 show comparative electrophoretic examples of using the focusing electrode assembly of FIG. 8 to separate sequenced M13 primers for T only on a MICROGENE BLASTER sequencer. The run length was 5 cm at 680 Volts (105 V per cm) at 50° C. using the protocol shown in Table 1. The run time was approximate 13 minutes long. FIG. 9 shows the electrophoresis run without applying voltage to the focusing electrode assembly of FIG. 8. FIG. 10 shows the electrophoresis run with applying 1.5 V between the elctrodes of the focussing electrode assembly of FIG. 8. In that case, 1.5 V was applied to the focusing electrodes, then 4 lanes of the gel were loaded at once using a ganged pipette. After waiting 5 seconds, 680 V was applied to the main gel electrodes for 30 seconds to run samples into the gel and stack the samples. Then the next 4 lanes were loaded in a similar manner. After the lanes were loaded, a voltage of 680 V was applied between the separation electrodes for approximately 13 minutes to separate the M13 DNA fragments. The resolutions in FIG. 10 which was obtained using focusing electrodes is visibly superior.

Figure 11:
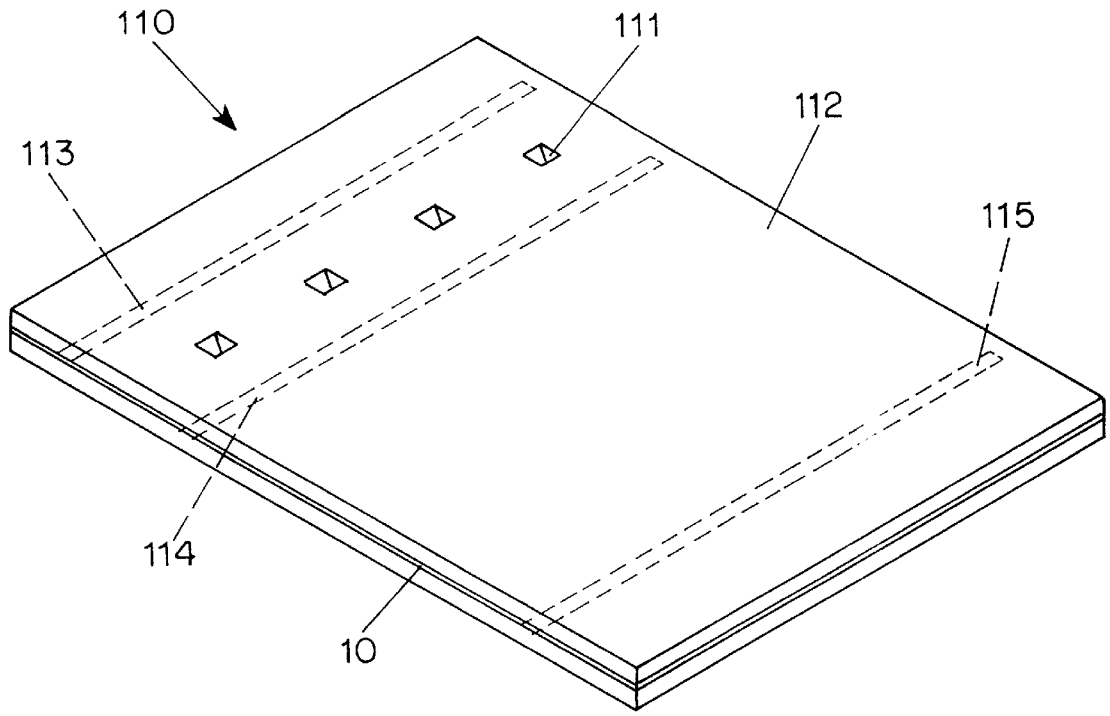
FIG. 11 shows a further embodiment of the invention.
Figure 12:
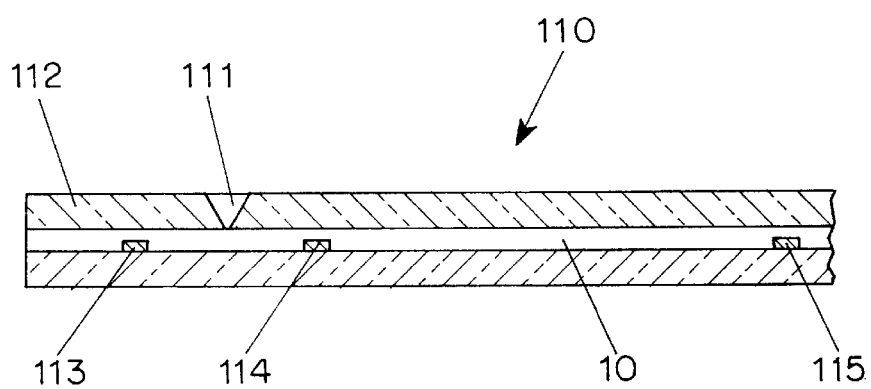
FIG. 12 shows a cross-section of the embodiment of FIG. 11.

FIGS. 11 and 12 show another embodiment of the present invention where the focusing electrodes are within the gel itself and no buffer is used. In this case, the sample DNA fragments to be focused and separated are loaded into the loading sites which are shown as a series of apertures 111 in the top glass plate 112 of the electrophoretic gel 110. Prior to separating the DNA fragments, a current is applied between focusing electrodes 113 and 114 to concentrate the DNA fragments near electrode 114. After a period of time is allowed to elapse (for example 30 sec.), a charge is given to the separation electrode 115 and electrode 114 such that the DNA fragments run down the gel toward electrode 115 and are separated.

It is contemplated that in such a gel as shown in FIGS. 11 and 12, the focusing process would occur partially or wholly within the gel, and could be incorporated with gels which do not require the use of buffer and thus do not have a buffer/gel interface. If necessary, it is contemplated that a seal such as an adhesive strip (not shown) could be applied to the top glass plate over the loading sites to prevent unwanted drying of the gel during a electrophoretic run.

TABLE 1

M13T 5.5
MASTER MIX:

| Reagents | Quantity |
| --- | --- |
| VGI sequencing buffer | 72 µl |
| M13 Univ. primer (3uM, Cy 5.5) | 36 µl |
| M13 s.s. DNA template (200 ng/µl) | 36 µl |
| 1/10 diluted thermosequenase | 90 µl |
| PCR water | 234 µl |
| T terminator | 468 µl |
| TOTAL | 936 µl |

1/10 diluted thermosequenase can be made as follows:
10 µl thermosequenase in 90 µl thermosequenase dilution buffer = 100 µl
Aliquot 30 ul/well and use the following sequencing reaction:

| | |
| --- | --- |
| 1) 94° C. for 2:00 min | 10) 94° C. for 15 sec. |
| 2) 1°/s to 94° C. | 11) 1.0°/s to 70° C. |
| 3) 94° C. for 15 sec. | 12) 70°C. for 1 min. |
| 4) 1.0°/s to 55° C. | 13) Go to 9, 14 times |
| 5) 55° C. for 15 sec. | 14) 4° C. forever |
| 6) 1°/s to 70° C. | 15) END |
| 7) 70° C. for 1 min. | |
| 8) Go to 2, 19 times | |
| 9) 1°/s to 94° C. | |

Add Formamide loading dye in a 5:4 ratio (M13T:dye) i.e. add 24 µl of dye per well

I claim:

1. A method for electrophoretic separation of analyte species in a sample, comprising the steps of:
    (a) loading the sample onto a loading site of an electrophoresis gel;
    (b) applying a focusing electric field using a first pair of electrodes to cause the analyte species to migrate to a narrow region disposed at or near the loading site to produce a focused sample; and
    (c) applying a separation electric field to cause the analyte species in the focused sample to migrate through the electrophoresis gel and to be separated into bands, wherein neither of the electrodes of the first pair of electrodes is used for applying the separation electric field.

2. The method of claim 1, wherein the electrophoresis gel has a plurality of loading wells, and wherein a removable electrode assembly comprising the first pair of electrodes mounted in a support is inserted into loading wells.

3. The method of claim 2, wherein the removable electrode assembly further comprises a sample-absorbing insert, and wherein sample is loaded onto the loading sites by absorbing the sample into the sample-absorbing insert and then inserting the electrode assembly into the loading wells.

4. An electrode assembly for use in focusing a sample prior to electrophoretic separation on an electrophoresis gel having a plurality of loading wells formed in the gel comprising:
    (a) an electrically insulating support member,
    (b) a first electrode affixed to the support member, said first electrode having a plurality of conductive extensions along a first edge which conform to the shape of the loading wells of the gel, and a second electrode affixed to the support member at a distance from the first electrode, wherein the electrodes are disposed with respect to each other such that when the electrode assembly is inserted into the sample wells and an electric field is generated between the first and second electrodes the sample in each well is concentrated near the first electrode.

5. The electrode assembly of claim 4, further comprising a plurality of absorptive sample collection members, one aligned with each conductive extension along the first edge of the first electrode.

6. The electrode assembly of claim 5, wherein the absorptive sample collection member is disposed between the first and second electrodes.

7. The electrode assembly of claim 4, further comprising a plurality of absorptive sample collection members, one aligned with each conductive extension along the first edge of the first electrode.

8. An article of manufacture for electrophoretic separation of analyte species in a sample, comprising first and second substrates disposed in parallel to one another and a layer of separation medium disposed between the first and second substrates, wherein the first and second substrates together define a loading well adjacent to a first end of the separation medium; and further comprising at least one focusing electrode disposed within the loading well or within the separation medium within 500 microns of the loading well.

9. The article of claim 8, wherein the article comprises at least two focusing electrodes, a first focusing electrode disposed in the loading well adjacent the first substrate and a second focusing electrode disposed in the loading well adjacent the second substrate.

10. The article of claim 9, further comprising at least a third focusing electrode disposed in the loading well adjacent the first substrate.

11. The article of claim 8, wherein the article comprises at least two focusing electrodes, a first focusing electrode disposed in the separation medium within 500 microns of the loading well, and a second focusing electrode disposed within the loading well.

12. The article of claim 8, wherein the article comprises at least first and second focusing electrodes disposed within the separation medium adjacent to the first substrate, said first focusing electrode being disposed closer to the loading well than the second focusing electrode.

13. The article of claim 12, wherein the article further comprises a third focusing electrode disposed within the separation medium adjacent to the first substrate.

14. The article of claim 12, wherein the article further comprises a third focusing electrode disposed in the separation medium adjacent to the second substrate and opposite the second focusing electrode.

15. The article of claim 12, wherein the article further comprises a fourth focusing electrode disposed in the separation medium adjacent to the second substrate and opposite the first focusing electrode.

16. An electrode assembly for use in focusing a sample prior to electrophoretic separation on an electrophoresis gel having a plurality of loading wells formed in the gel comprising:

(a) an electrically insulating support member, (b) a first electrode affixed to the support member, said the first electrode having a plurality of conductive extensions along a first edge which conform to the shape of the loading wells of the gel, (c) a second electrode affixed to the support member at a distance from the first electrode, wherein the electrodes are disposed with respect to each other such that when the electrode assembly is inserted into the sample wells and an electric field is generated between the first and second electrodes the sample in each well is concentrated near the first electrode, and (d) a plurality of absorptive sample collection members, wherein one absorptive sample collection member is aligned with each conductive extension along the first edge of the first electrode, and is disposed between and in electrical contact with the first and second electrodes.

* * * * *